United States Patent
Kehr

(10) Patent No.: US 7,056,285 B2
(45) Date of Patent: Jun. 6, 2006

(54) APPARATUS FOR POSITIONING AT LEAST ONE COMPONENT WITHIN AN ENDOSCOPIC SYSTEM

(75) Inventor: Ulrich Kehr, Leinfelden-Echterdingen (DE)

(73) Assignee: Karl Storz GmbH & Co. KG (DE)

( * ) Notice: Subject to any disclaimer, the term of this patent is extended or adjusted under 35 U.S.C. 154(b) by 322 days.

(21) Appl. No.: 10/763,544

(22) Filed: Jan. 23, 2004

(65) Prior Publication Data

US 2004/0152950 A1    Aug. 5, 2004

Related U.S. Application Data

(63) Continuation of application No. PCT/EP02/07140, filed on Jun. 28, 2002.

(30) Foreign Application Priority Data

Jul. 24, 2001    (DE) ................ 101 36 998

(51) Int. Cl.
*A61B 1/06* (2006.01)
(52) U.S. Cl. ..................... 600/163; 600/160
(58) Field of Classification Search ............. 600/160, 600/162, 163, 167, 168, 112; 359/824, 694, 359/814, 822, 704

See application file for complete search history.

(56) References Cited

U.S. PATENT DOCUMENTS

| 5,056,902 A | 10/1991 | Chinnock et al. | 359/503 |
| 5,359,992 A | 11/1994 | Hori et al. | 128/4 |
| 5,978,161 A | 11/1999 | Lemke | 359/824 |
| 6,522,477 B1* | 2/2003 | Anhalt | 359/694 |
| 6,537,210 B1* | 3/2003 | Wulfsberg | 600/173 |
| 6,616,602 B1* | 9/2003 | Witte | 600/167 |
| 6,632,173 B1* | 10/2003 | Kehr et al. | 600/167 |
| 2002/0049366 A1 | 4/2002 | Kehr | 600/172 |

FOREIGN PATENT DOCUMENTS

| DE | G 88 10 004.8 | 12/1988 |
| DE | 42 11 203 | 10/1993 |
| DE | 195 21 654 | 12/1996 |
| DE | 197 18 189 | 11/1997 |
| DE | 197 13 276 | 10/1998 |
| DE | 199 27 816 | 1/2001 |
| JP | 58208721 | 12/1983 |
| WO | WO 00/45210 | 8/2000 |

\* cited by examiner

*Primary Examiner*—Beverly M. Flanagan
(74) *Attorney, Agent, or Firm*—St. Onge Steward Johnston & Reens LLC

(57) ABSTRACT

A description is given of an apparatus for positioning at least one component within an endoscopic system, having a hermetically tight housing, having at least one external magnetically active element which is arranged outside the housing, and having at least one internal magnetically active element which is arranged inside the housing, a magnetic force coupling acting through the housing between the external element and the internal element, it further being possible for the external element and the internal element to move at least with an axial movement component with reference to a longitudinal axis of the housing, and the internal element being in operational connection with the component in such a way that a movement of the internal element causes a movement of the component. The at least one internal element is arranged hanging, at least with an axial movement component via a holder in the housing with reference to the direction of the attractive force of the external element, a side, facing the external element, of the internal element is free, the component being connected to the internal element via a driver element in such a way that the component is axially displaced given an axial movement of the internal element.

11 Claims, 5 Drawing Sheets

APPARATUS FOR POSITIONING AT LEAST ONE COMPONENT WITHIN AN ENDOSCOPIC SYSTEM

CROSS REFERENCE TO PENDING APPLICATION

The present application is a continuation of International Patent Application PCT/EP02/07140 filed on Jun. 28, 2002 which designates the United States, and which claims priority of German Patent Application 101 36 998.0 filed on Jul. 24, 2001.

BACKGROUND OF THE INVENTION

The invention relates to an apparatus for positioning at least one component within an endoscopic system, comprising a hermetically tight housing, at least one external magnetically active element which is arranged outside the housing, and at least one internal magnetically active element which is arranged inside the housing, a magnetic force coupling acting through the housing between the external element and the internal element, it further being possible for the external element and the internal element to move at least with an axial movement component with reference to a longitudinal axis of the housing, and the internal element being in operational connection with the component in such a way that a movement of the internal element causes a movement of the component.

In the sense of the present invention, the term component comprises, for example, optical components, for example lenses with or without a mounting in an optical head of an endoscope. Such an optical component can be, for example, part of a focusing device of an endoscope for focusing the endoscopic image. However, mechanical components also come under the term of components.

In the sense of the present invention, endoscopic systems are understood as endoscopes, or else endoscopic camera systems.

In the sense of the present invention, a hermetically tight housing is understood as a housing sealed in such a way that it can be autoclaved, for example, without there being the risk that, in conjunction with the extreme temperature fluctuations, dampness or liquids, and therefore contaminations, can penetrate into the interior of the housing.

In the sense of the present invention, a magnetically active element is understood as a magnet, for example a permanent. magnet, or else an element or material which can be magnetized under the influence of a magnetic field, or else an electromagnet. Thus, for example, the at least one external magnetically active element can be a permanent magnet, and the at least one internal magnetically active element can be a magnetizable ferromagnetic material or element, or vice versa. It is sufficient if the at least one external magnetically active element or the at least one internal magnetically active element generates a magnetic field, and the respective other element then cooperates in a magnetically force-coupled fashion under the influence of this magnetic field with the element generating the magnetic field. The magnetic force coupling between the at least one external magnetically active element and the at least one internal magnetically active element acts in this case through the housing, as a result of which a so-called magnetic coupling is implemented.

From German Utility Model DE 88 10 044 U1, an apparatus for positioning at least one component within an endoscopic system is known having the at least one external magnetically active element arranged on the inside of an external ring arranged concentrically about the housing axis, and the at least one internal magnetically active element is guided in the form of an annular magnet inside the housing in a slideway, and is fixedly connected to the component to be positioned. The external ring, which carries the external magnetically active element, serves as an actuating element, and rotating the ring axially moves the ring, and thus the external magnetically active element, along a screw guide, as a result of which the internal magnetically active element is likewise moved axially. In this known apparatus, the external magnetically active element and the internal magnetically active element extend over the entire circumference about the longitudinal axis of the housing. Such an arrangement of these elements over the entire circumference can compensate the radial attractive force between the internal and external elements in such a way that the internal element is not pressed against a sliding seat subject to friction, something which would cause an increased frictional grip during the axial movement of the internal element, as a result of which the axial movement of the internal element, and thus of the component to be positioned, could not be performed without jerking. However, the arrangement of the external and internal elements over the entire circumference entails an increased outlay on costs for the apparatus. If the external magnetically active element and the internal magnetically active element were to extend only over a partial circumference of the housing of the apparatus, there would, by contrast, be the disadvantage that the radial attractive force between the elements would not be compensated for and this would lead in the case of a sliding guidance for the internal and/or external elements to increased friction during their movement, as a result of which it would be impossible to ensure positioning of the at least one component without jerking.

Another design of an apparatus for positioning components within endoscopic systems is disclosed in DE 197 13 276 A1, in the case of which a plurality of external magnetically active elements are arranged on an annular element arranged outside the housing concentrically with the housing axis, and a plurality of internal magnetically active elements are arranged on an annular element arranged inside the housing, likewise concentrically with the housing axis. Both the external annular element and the internal annular element are rotatable, but axially undisplaceable. In order by rotating the external annular element to achieve an axial movement of the at least one component to be positioned, the internal ring is mechanically connected to the component via a type of gear in the form of a helical groove in order to transmit the rotation of the external ring into a translatory movement of the component. The lead of the helical groove in this case determines the ratio between the rotational angle of the external annular element and the displacement travel of the component to be positioned. However, the lead cannot be selected arbitrarily, in particular it is bounded above because otherwise self-locking of the gear occurs. Particularly in the case of large leads of the helical groove, the friction can interfere in a jerky movement. Consequently in practice it is necessary to select the lead such that the external annular element must always be rotated by a relatively large angle in order to obtain a comparatively small translatory movement. However, this is disadvantageous in the case of apparatuses, for example focusing devices, in which large adjusting travels are to be quickly handled.

From U.S. Pat. No. 5,359,992 an apparatus for positioning components within endoscopic systems is known, in the case of which there are constructed diametrically opposite in an external annular element, which is arranged, in turn, concentrically with the housing axis and around the housing, two helical slots in which round magnets are inserted diametrically opposite one another. The round magnets engage into an axially extending cutout on the outside of a sleeve arranged in the ring. A rotation of the external ring therefore causes an axial displacement of the external magnet. Magnets situated diametrically opposite in a corresponding fashion are present in the internal sealed region and track the movements of the external magnet and thus effect the coupling. A disadvantage of this configuration is the areal slideway, heavily subject to friction, of the internal magnets and even here, also, of the external magnets.

The same problem exists in the case of the apparatus known from U.S. Pat. No. 5,056,902 for positioning components inside endoscopic systems, which serves there as a focusing device. In the above-named known apparatuses, in which both the external magnetically active element and the internal magnetically active element can be displaced at least with axial movement components, the disadvantages consist in a slideway which is subject to friction and has an areal bearing surface of the at least one internal magnetically active element, which bearing surface is heavily subject to friction because of the attraction between the external element and the internal element. However, because the slideway of the at least one internal magnetically active element inside the housing is subject to friction, jerky movements of the at least one component occur from time to time when it is being positioned, since the not inconsiderable static friction of the internal magnetically active element must be overcome at the start of each axial movement of the at least one external magnetically active element. Because of this, however, exact positioning of the at least one component is not always ensured.

In the case of the known apparatuses, the friction in the movement of the magnetically active elements can be reduced only by configuring the elements over the entire circumference, or at least by a rotationally symmetrical arrangement of the elements, and this in turn is associated with an increased outlay on construction.

It is therefore the object of the invention to improve an apparatus of the type mentioned at the beginning to the effect that, in conjunction with a design of low complexity, the magnetic coupling permits the at least one component to be positioned as far as possible without jerking.

SUMMARY OF THE INVENTION

According to the invention, an apparatus for positioning at least one component within an endoscopic system is provided, comprising:

a hermetically tight housing having a longitudinal axis;

at least one external magnetically active element arranged outside said housing and movable at least with an axial movement component with reference to said longitudinal axis of said housing;

at least one internal magnetically active element arranged inside said housing and movable at least with an axial movement component with reference to said longitudinal axis of said housing, said internal magnetically active element being in operational connection with said component in such a way that the movement of said internal magnetically active element causes a movement of said component;

a magnetic force coupling acting through said housing between said external magnetically active element and said internal magnetically active element;

wherein said at least one internal magnetically active element is arranged, via a holder in said housing, hanging with reference to a direction of an attractive force of said external element and at least with an axial movement component, wherein a side, facing said external magnetically active element, of said internal magnetically active element is free, and wherein said component is in operational connection with said internal magnetically active element via a driver element in such a way that said component is axially displaced given an axial movement of said internal magnetically active element.

The apparatus according to the invention is therefore based on the principle of suspending the at least one internal magnetically active element with reference to the direction of the attractive force of the external element in an axially moveable fashion, instead of arranging the internal element in slideways such as grooves or the like. The holder therefore absorbs the attractive force acting in the direction of the external magnetically active element, while the internal element is free on its side facing the external element, in other words is arranged "floating" or "flying" in the housing. In the case of its axial movement, the internal element is therefore not subject to frictional forces as in an areal slideway, which can be dispensed with here. Thus, also the at least one component to be positioned, which is in operational connection with the internal element only via a driver element, is not subject to the attractive force of the external element, the result also being that the component can be displaced within the housing with a particularly low degree of friction when the internal element is moved axially. Moreover, owing to the suspension of the internal element it is possible in a particularly advantageous way to provide an arrangement of the internal and the external magnetically active elements which is asymmetric with reference to the housing axis, since no compensation of the radial attractive force is required, it thereby being possible to reduce the outlay on parts and therefore on costs for the apparatus according to the invention. Moreover, the inventive design of the apparatus renders it possible to provide, instead of an external annular element known in the prior art and arranged concentrically with the housing axis, a lateral adjusting wheel for actuating the magnetic coupling, as a result of which large adjusting travels of the component can be handled quickly. The suspension of the at least one internal element can be accomplished, for example, in the form of gliding rollers or the like, or by a holder, suspended in an articulated fashion in the manner of a pendulum.

It is particularly preferred when the internal element is suspended in pendulum fashion in the housing about at least one swivel axis by means of the holder.

The advantage of this measure consists, firstly, in that in conjunction with a pendulum suspension of the at least one internal element about at least one swivel axis there is achieved an axial mobility of the internal element which is particularly low in friction and in the case of which the attractive forces of the magnetically active elements are absorbed solely by the at least one swivel axis, and in that, secondly, a structurally simple, and therefore very cost-effective, design is attained.

In a further preferred refinement, the component is guided in an axially linear fashion in a guide.

It is possible by means of this measure to implement a guidance of the component inside the housing which is particularly favorable in frictional terms on the basis of the design according to the invention of the magnetic coupling, in accordance with which the at least one internal element is suspended in a freely moveable fashion in the housing, and the component has not to absorb any sort of radial forces via the driver element because of the operational connection with the internal element. Owing to the driver element, only axial forces act on the component, the result being to achieve a guidance of the component which is particularly low in friction.

In a further preferred refinement, the holder is suspended with a first end via at least one joint in the housing, and carries the internal element at the opposite end.

This measure constitutes a structurally particularly simple configuration for the suspension of the internal element, which is of a pendulum type in accordance with a previously mentioned refinement. In this case, the holder can advantageously extend diametrically through the internal cross section of the housing, the result being that substantially the entire inside diameter of the housing is available, and so a large travel movement of the internal element can be attained even in the case of small deflections of the holder about the at least one swivel axis.

It is preferred in this case when the internal element is connected in an articulated fashion to the holder in such a way that the angular position of the internal element does not change with reference to the longitudinal axis of the housing during the pendulum movement.

This measure is particularly advantageous in the case of very large adjusting travels and thus large deflections of the holder from its rest position, since owing to this measure the orientation between the internal element and the external element does not vary, and thus the magnetic force coupling between these two elements is substantially preserved even in the case of large, adjusting travels and large deflections of the holder.

In a further preferred refinement, the holder extends on a side of the component.

This measure achieves the advantage of a configuration of the apparatus according to the invention which is particularly space saving and takes up little room, it being possible with this refinement for the holder to extend substantially over the entire inside diameter of the housing. This arrangement is particularly advantageous whenever the handling of the positioning apparatus and the component are arranged axially closely to one another or even at the same level.

In a further preferred refinement, the holder is in operational connection with the component via the driver element with radial play relative to the longitudinal direction of the housing.

This measure is advantageous within the scope of the pendulum-like configuration of the holder, since in the case of such a pendulum-like configuration of the holder the latter not only has a movement component in the longitudinal direction of the housing axis, that is to say axially, but also has a radial movement component about the at least one swivel axis in accordance with the swivelling. The abovementioned measure now advantageously has the effect that because of the radial play between the holder and the component no radial constraining forces are transmitted to the component via the connection by the driver element through the radial movement component of the holder, and so the said component can continue to be displaced at a low level of friction, particularly in the linear guide.

In a further preferred refinement, the component is axially spaced from the holder, and the driver element is designed as an elongated pulling and pushing element which is connected, on the one hand, to the holder and, on the other hand, to the component, preferably in an articulated fashion in each case.

This measure is advantageous whenever the component to be positioned is arranged in the distal region, whereas the aim is to perform the handling of the positioning device at the proximal end of the endoscopic system, for example for ergonomic reasons. In this case, as well, the refinement according to the invention attains a positioning of the at least one component which has a low level of friction and thus is not jerky.

In a further preferred refinement, the external element is connected to an operating element which is arranged on a side of the housing.

This measure, which is rendered possible chiefly by the configuration according to the invention of the magnetic coupling of the present apparatus, has the advantage of an ergonomically particularly favorable handling of the apparatus, while in the case of the apparatuses known from the prior art the operating element is always designed in the form of an adjusting ring arranged around the housing concentrically with the housing axis. The advantage of an operating element arranged on this side of the housing consists in that it permits one-handed operation, that is to say the apparatus can be operated, for example, with the thumb of the same hand which is holding the endoscopic, system in order to position the at least one component. The operating element can be designed, for example, in the form of a slide.

However, it is preferred when the operating element is designed as an adjusting wheel which has an axis of rotation running approximately transverse to the longitudinal axis and is in operational connection with the external element, a rotary movement of the adjusting wheel causing a movement of the external element with an axial movement component.

Such a configuration of the operating element has the advantage of a particularly ergonomically favorable handling of the apparatus according to the invention by virtue of the fact that the adjusting wheel can be actuated with the thumb. Particularly in connection with the magnetic coupling according to the invention of the present apparatus, it is possible to implement such an ergonomically favorable operating element in conjunction with an endoscopic system which can be autoclaved on the basis of the magnetic coupling according to the invention.

Further advantages and features will become apparent from the following description and the attached drawings.

It goes without saying that the previously mentioned features and those still to be explained below can be used not only in the respectively specified combination, but also in other combinations or on their own without departing from the scope of the present invention.

BRIEF DESCRIPTION OF THE DRAWINGS

Exemplary embodiments of the invention are illustrated in the drawings and described in more detail below with reference thereto. In the drawings.

DETAILED DESCRIPTION OF PREFERRED EMBODIMENTS

Figure 1:
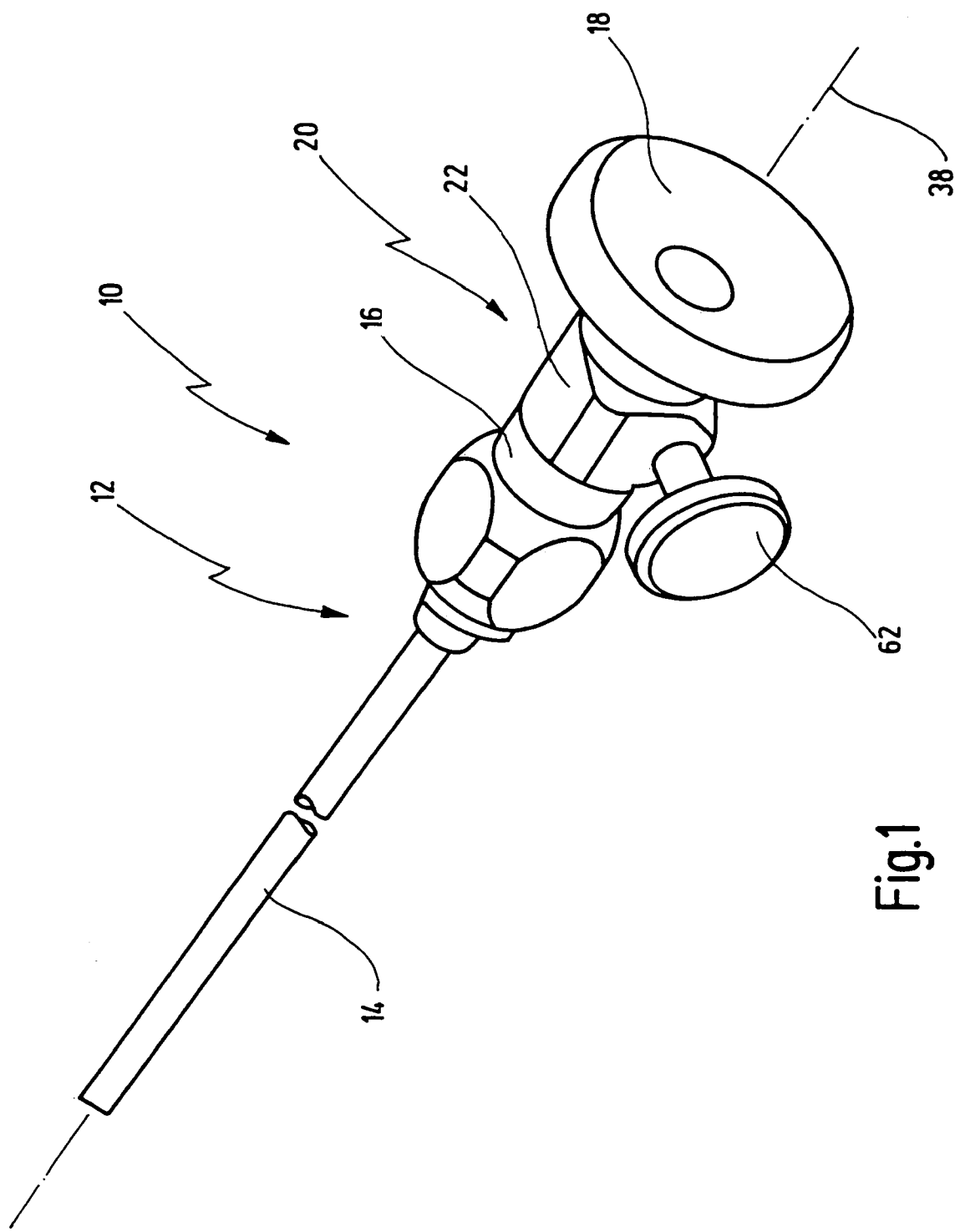
FIG. 1 shows an endoscopic system in a perspective overall illustration, an apparatus for positioning at least one component according to the invention being present therewith.

An endoscopic system provided with the general reference numeral 10 is illustrated in FIG. 1. The endoscopic system 10 is an endoscope 12 in the exemplary embodiment shown.

The endoscope 12 has a shaft 14 which is connected at the proximal end to an optics head 16 at whose proximal end an eyepiece or an eyecup 18 is arranged. Running in the shaft 14 and through the optics head 16 is an image transmission system (not illustrated in more detail) which is designed as a rod lens system whose proximal end is provided in FIG. 2 with the reference numeral 19.

Also present in the endoscope 12 is an apparatus 20 for positioning at least one component within the endoscope 12 and which is described in more detail below with reference to FIG. 1 and FIG. 2.

The apparatus 20 has a hermetically tight housing 22 which is substantially of hollow cylindrical design. The housing 22 is part of the optics head 16. While the housing 22 is wholly continuous in the circumferential direction, that is to say has no openings or cutouts, the housing 22 is sealed in a hermetically tight fashion at the eyepiece end and also tightly sealed at the shaft 14 end such that the apparatus 20 is hermetically tight and therefore autoclavable.

A component 24 to be positioned is arranged within the housing 22. The component 24 is designed here as a mounting for a plurality of lenses 26 which serve the purpose by means of appropriate axial displacement of position, as will be explained in more detail hereafter, of focusing the endoscopic image transmitted by the image transmission system.

The component 24 is constructed overall like a sleeve and has a distal end 28 and a proximal end 30.

The component 24 is guided in an axially linear fashion in a guide 32 which is designed as a sleeve and has a distal guide portion 34, in which the distal end 28 of the component 24 is guided in an axially linear fashion, and a proximal guide portion 36, in which the proximal end 30 of the component 24 is guided in an axially linear fashion.

Consequently, the component 24 is guided in an axially linear fashion within the guide 32 and, if appropriate, secured against rotation about a longitudinal axis 38.

The longitudinal axis 38 forms the longitudinal axis of the shaft 14 and also the longitudinal axis of the housing 22 and the apparatus 20.

The apparatus 20 further has at least one external magnetically active element 40, for example a permanent magnet which is arranged outside the housing 22. In the present exemplary embodiment, the external magnetically active element 40 is integrated in a thickened section 42 of the housing 22, it likewise being understood in this regard that the element 40 is arranged outside the housing 22. Present in the thickened section 42 is an appropriate cutout 44 in which the element 40 is arranged. As follows from FIG. 2, the housing 22 separates the exterior of the housing 22 from the interior of the housing 22 in a hermetically tight fashion in the region of the cutout 44, as well.

The external magnetically active element 40 can be moved at least with an axial movement component in accordance with a double arrow 46.

The apparatus 20 also has at least one internal magnetically active element 48 which is arranged within the housing 22 and is arranged opposite the external element 40.

The external element 40 and the internal element 48 extend only over a partial extent of the housing 22.

The internal magnetically active element 48, for example likewise a permanent magnet or simply a magnetizable material, for example a ferromagnetic material, is correspondingly connected to the external element 40 via a magnetic force coupling, the magnetic force coupling acting through the hermetically tightly sealed housing 22 which correspondingly does not shield the magnetic field. The magnetic force coupling consists in that the internal and the external elements 40 and 48 attract one another mutually.

The internal magnetically active element 48 can also be moved at least with an axial movement component, as is still to be explained hereafter.

The internal element 48 is arranged or fastened on a holder 50, it also being possible for the internal magnetically active element 48 to consist of a portion, for example a magnetizable one, of the holder 50.

Via the holder 50, the internal magnetically active element 48 is arranged hanging in the housing 22 with reference to the direction of the attractive force of the external element 40, which runs essentially transverse to the longitudinal axis 38 or radially with reference to the latter through the housing 22.

The holder 50 extends essentially transverse to the longitudinal axis 38 of the housing 22 and is fastened via at least one joint 54 on the housing 22 with one end 52 which is situated opposite the respective end of the holder 50, at which the internal magnetically active element 48 is arranged, specifically indirectly via a bearing part 56, which is for its part fixedly connected to the housing 22, in the exemplary embodiment shown.

In the exemplary embodiment shown, the joint 54 consists simply in that the end 52 of the holder 50 is suspended in the bearing part 56 and, through appropriate shaping of the end 52, forms in the bearing part 56 a bearing point about which the holder 50 can oscillate or swivel. The joint 54 correspondingly forms a swivel axis about which the holder 50 is suspended in a pendulum fashion in the housing 22.

In the present exemplary embodiment, the holder 50 is designed in the form of a ring, the component 24 passing through the holder 50.

Figure 2:
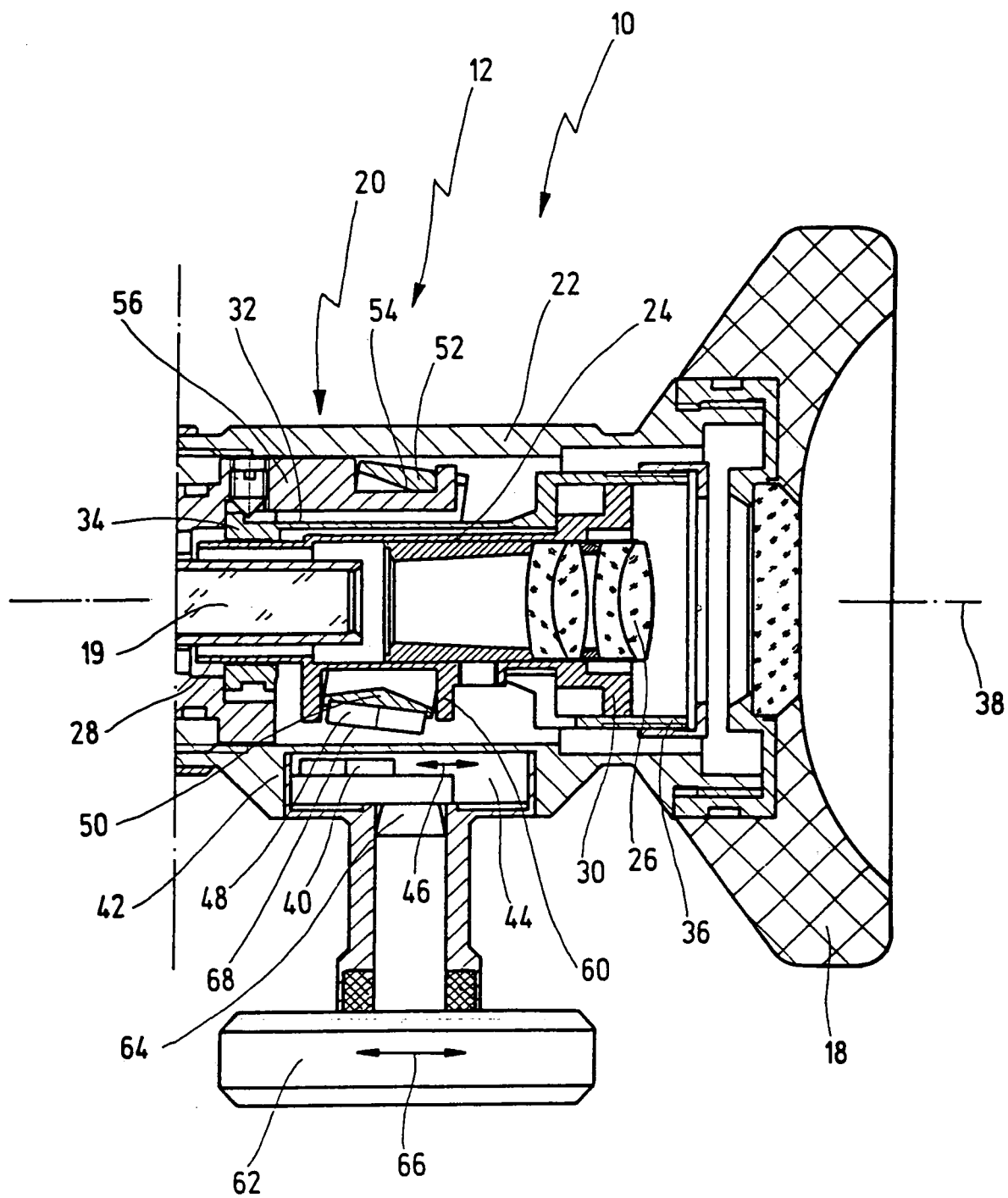
FIG. 2 shows a longitudinal section, enlarged by comparison with FIG. 1, through the proximal end of the endoscopic system in FIG. 1, in which the positioning apparatus is arranged.

As further follows from FIG. 2, the holder 50 extends with reference to the mechanical line of action between its suspension at the end 52 and the opposite end, at which the internal element 48 is arranged, essentially diametrically through the interior of the housing 22 and parallel to the direction of action of the attractive force exerted on the internal element 48 by the external element 40. More precisely, this line of action is aligned with the attractive force in the position where the holder 50 is not pivoted out, as a result of which the joint 54 can absorb the attractive force optimally.

The element 24 is in operational connection with the internal magnetically active element 48 via a driver element 60, the driver element 60 being designed in the form of two projections which protrude radially from the component 24 and engage the holder 50.

In the event of a deflection of the holder 50 about the swivel axis formed by the joint 54, the component 24 is correspondingly displaced linearly in the guide 32 in the direction of the longitudinal axis 38.

The holder 50, and thus the internal element 48, is connected in this arrangement to the component 24 via the driver element 60 with a radial play with reference to the longitudinal axis 38 of the housing 22, and this is achieved in the exemplary embodiment shown by the simple abutment of the driver element 60 in the form of the two radially protruding projections on the holder 50.

It goes without saying that the joint provided with the reference numeral 54 is not only to be understood to the effect that such a joint defines a rigid swivel axis, but that it could also implement a suspension of the holder 50 via a flexible element in the housing 22, it likewise being possible to understand this as an articulated connection with the housing 22 which defines a swivel axis, such a swivel axis not requiring to be sharply defined in space. Again, the holder 50 could have a plurality of suspension points which are formed by a plurality of joints.

As becomes apparent from FIG. 2, the external magnetically active element 40 and the internal magnetically active element 48 form an asymmetric arrangement with reference to the longitudinal axis 38 of the housing 22, because they extend only over a partial extent of the housing 22, and this has the advantage that, as illustrated in FIG. 2, it is possible to provide an operating element 62 arranged on the side of the housing 22 for the purpose of the axial movement of the external element 40. The operating element 62 is designed in the form of an adjusting wheel whose axis of rotation runs transverse to the longitudinal axis 38. The adjusting wheel is fixedly connected to the external element 40 via a pin 64. A rotary movement of the adjusting wheel in a direction in accordance with a double arrow 66 in this case causes a swivelling movement of the external element 40 about the axis of rotation of the adjusting wheel with an axial movement component in the corresponding direction of the double arrow 46.

The circumferential extent of the internal element 48 is adapted appropriately to the swivel radius of the external element 40 in order always to ensure a magnetic force coupling between the two elements 40, 48.

The adjusting wheel could also be connected to the external element 40 via a gear which converts a rotary movement of the adjusting wheel into an exclusively axially linear movement of the external element 40.

As further follows from FIG. 2, the internal magnetically active element 48 is suspended in the housing 22 in such a way that its end 68 facing the external element 40 is free, that is to say is not subject to friction.

Figure 3:
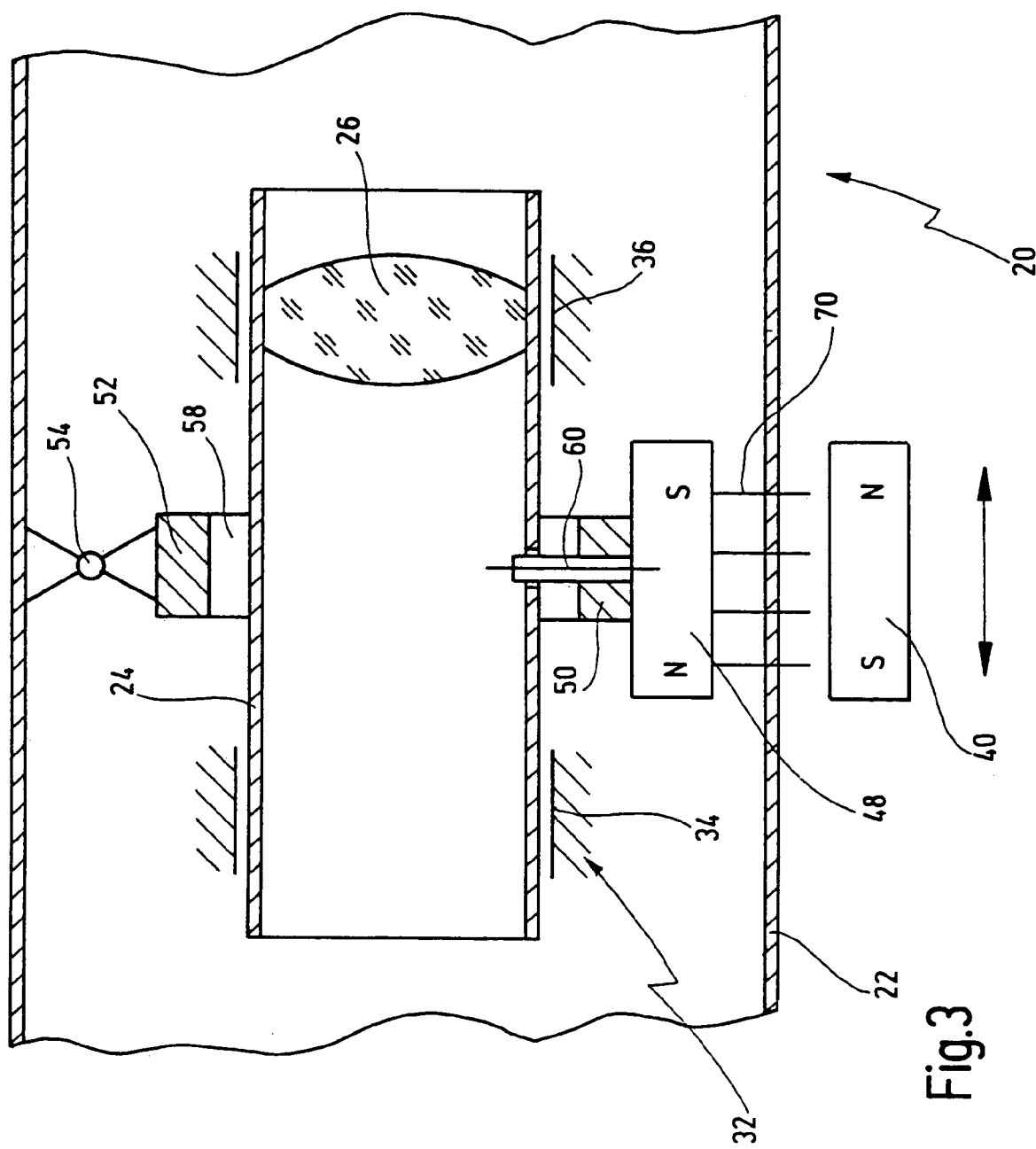
FIG. 3 shows the functional principle of the positioning apparatus in accordance with FIG. 2 in a simplified diagrammatic illustration of a longitudinal section, in a first operating state.
Figure 4:
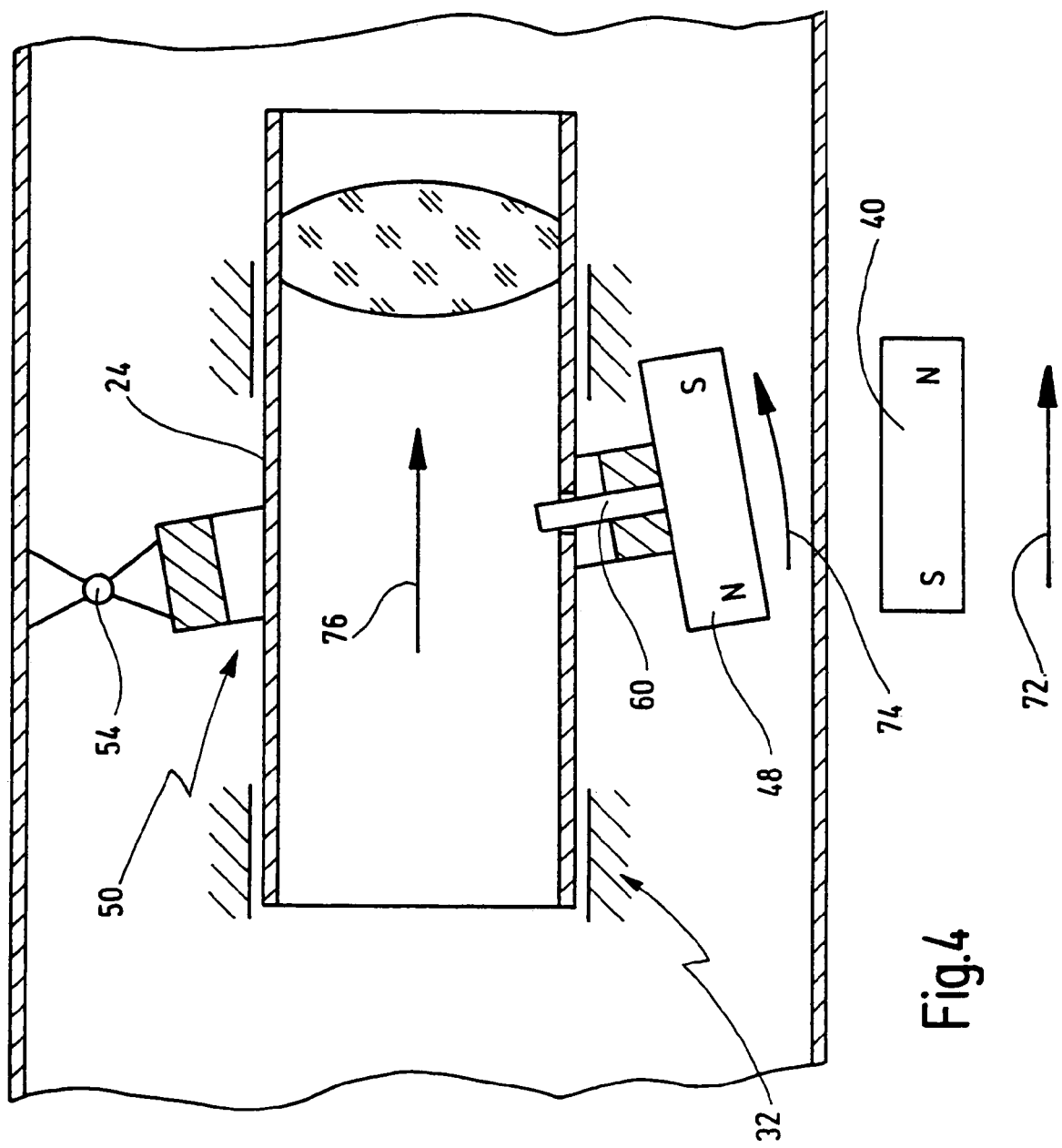
FIG. 4 shows a diagrammatic illustration, comparable with FIG. 3, in a second operating position of the positioning apparatus.

The functional principle of the apparatus 20 is explained in more detail with the aid of the diagrammatically simplified illustration in FIGS. 3 and 4, the elements taken over in FIGS. 3 and 4 from FIG. 2 being provided with the same reference numerals.

The apparatus 20 is shown in FIG. 3 in an operating position in which the holder 50, and thus the internal magnetically active element 48, are not deflected with reference to their suspension in the joint 54.

The magnetic attractive force, illustrated in FIG. 3 by arrows 70, exerted by the external magnetically active element 40 on the internal element 48 is absorbed solely by the joint 54, while the internal magnetically active element 48 is suspended in the housing 22 in a floating or flying fashion. The internal magnetically active element 48 and also the holder 50 are correspondingly not subjected to any sort of sliding friction.

The component 24, which is in operational connection with the internal magnetically active element 48 via the driver element 60, which is illustrated in FIGS. 3 and 4 simply as a pin which engages in an opening in the component 24, without being fixedly connected to the latter, that is to say has a radial play with reference to the component 24, is correspondingly guided linearly in the guide 32 in a fashion essentially free from radial forces. The attractive force between the elements 40 and 48 thus in no way acts to increase friction on the guidance of the component 24 in the guide 32.

If, as illustrated in FIG. 4, the external magnetically active element 40 is moved axially in the direction of an arrow 72, the internal magnetically active element 48 is deflected like a pendulum with an axial movement component via the magnetic force coupling to the external element 40 about the pivot axis, defined by the joint 54, in the direction of an arrow 74, and the component 24 is correspondingly linearly displaced in the guide 32 via the driver element 60, as a result of which the component 24 is positioned or adjusted in position as desired. Since there is essentially no static friction to be overcome, the positioning of the component 24 correspondingly takes place without jerking and with extremely little friction.

Because the component 24 is connected with radial play to the internal magnetically active element 48 via the driver element 60, the radial movement component of the internal magnetically active element 48 also does not act on the movement of the component 24 in the guide 32 in a fashion which increases friction or disturbs, but what happens is only the movement component of the element 48 is transmitted in the direction of the longitudinal axis 38 in accordance with an arrow 76 in FIG. 4.

In order to keep constant, over the swivelling range, the angular position of the internal element 48 during its deflection from the position of rest about the swivel axis defined by the joint 54, the internal element 48 could also be appropriately connected in an articulated fashion to the holder 50, or the holder 50 could be designed as an articulated parallelogram such that the internal element 48 runs in each angular position parallel to the external element 40.

Figure 5:
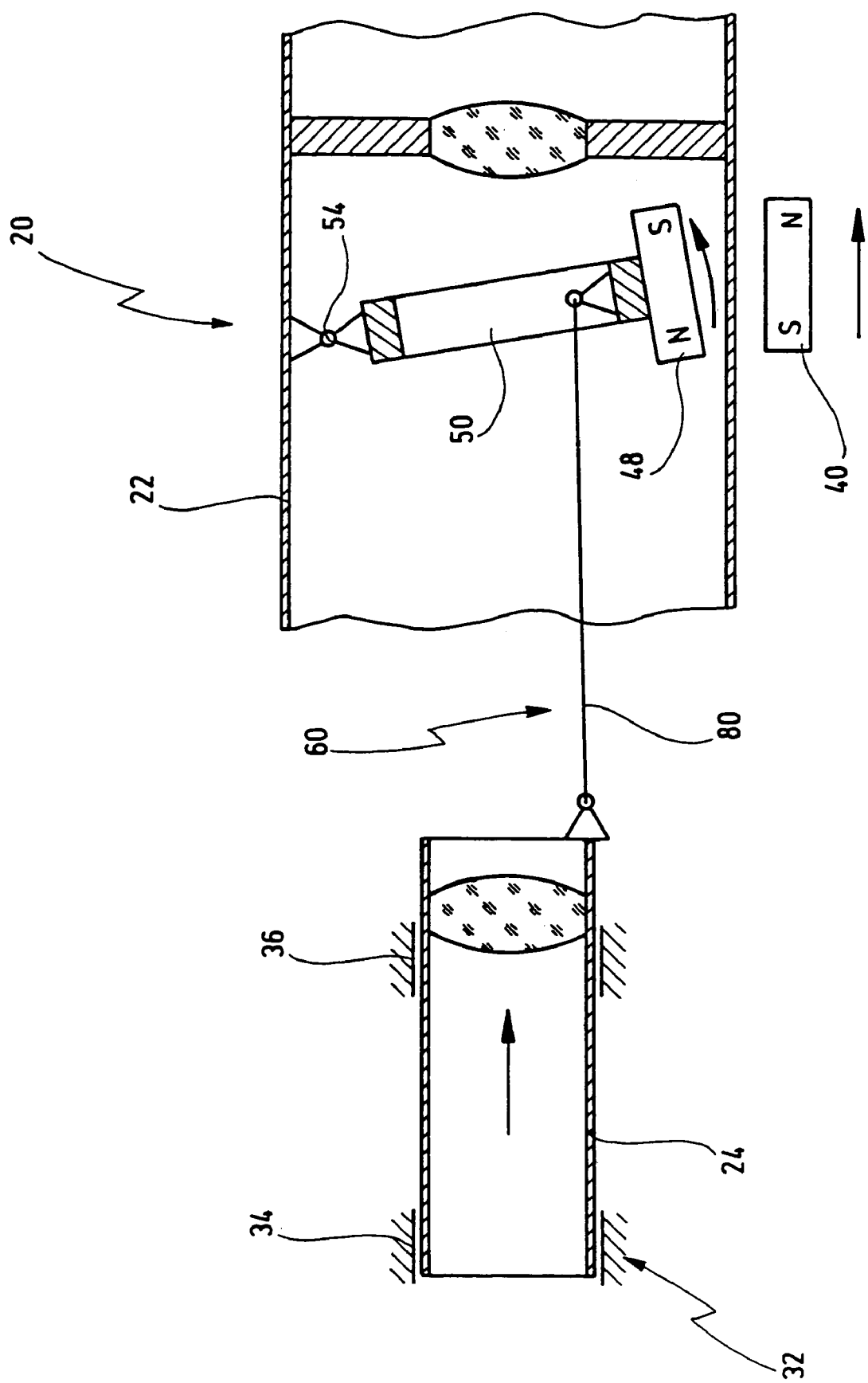
FIG. 5 shows a further exemplary embodiment of a positioning apparatus in a likewise diagrammatic illustration.

FIG. 5 illustrates an exemplary embodiment of the apparatus 20 which is slightly modified by comparison with the previous exemplary embodiment in accordance with FIGS. 1 to 4, and in this case the component 24 is axially spaced from the holder 50. The driver element 60 is designed in this case as an elongated pulling and pushing element 80 which is connected to the holder 50, on the one hand, and to the component 24, on the other hand. In the exemplary embodiment shown, the pulling and pushing element 80 is connected in an articulated fashion both to the component 24 and to the holder 50, in order to create a compensation for the radial movement component of the internal magnetically active element 48 or the holder 50 during its pendulum-like swivelling about the joint 54.

The embodiment of the apparatus 20 shown in FIG. 5 is suitable for the case when the component 24 to be positioned is arranged in a distal fashion in the endoscopic system, while the operation of the apparatus 20 is intended to be performed proximally at the endoscopic system.

What is claimed is:

1. An apparatus for positioning at least one component within an endoscopic system, comprising:

a hermetically tight housing having a longitudinal axis;

at least one external magnetically active element arranged outside said housing and movable at least in an axial direction with reference to said longitudinal axis of said housing;

at least one internal magnetically active element arranged inside said housing and movable at least in an axial direction with reference to said longitudinal axis of said housing, said at least one internal magnetically active element being in operational connection with said component in such a way that the movement of said at least one internal magnetically active element causes a movement of said component;

a magnetic force coupling acting through said housing between said at least one external magnetically active element and said at least one internal magnetically active element wherein said at least one internal magnetically active element is arranged, via a holder in said housing, hanging with reference to a direction of an attractive force of said at least one external magnetically active element and at least with an axial direction, wherein a side, facing said at least one external magnetically active element, of said at least one internal magnetically active element is free, and wherein said component is in operational connection with said at least one internal magnetically active element;

a driver element connecting said component and said at least one internal magnetically active element in such a way that said component is axially displaced given an axial movement of said at least one internal magnetically active element.

2. The apparatus of claim 1, wherein said at least one internal magnetically active element is suspended in pendulum fashion in said housing about at least one swivel axis by means of said holder.

3. The apparatus of claim 1, wherein said component is guided in an axially linear fashion in a guide.

4. The apparatus of claim 1, wherein said holder is suspended with a first end via at least one joint in said housing, and carries said at least one internal magnetically active element at an end opposite to said joint.

5. The apparatus of claim 1, wherein said at least one internal magnetically active element is connected in an articulated fashion to said holder in such a way that an angular position of said at least one internal magnetically active element does not change with reference to said longitudinal axis of said housing.

6. The apparatus of claim 1, wherein said holder extends on a side of said component.

7. The apparatus of claim 1, wherein said at least one internal magnetically active element is in operational connection with said component via said driver element with radial play relative to said longitudinal axis of said housing.

8. The apparatus of claim 1, wherein said component is axially spaced from said holder, and wherein said driver element is designed as an elongated pulling and pushing element which is connected, on the one hand, to said holder and, on the other hand, to said component.

9. The apparatus of claim 8, wherein said pulling and pushing element is connected to at least one of said holder and said component in an articulated fashion.

10. The apparatus of claim 1, wherein said at least one external magnetically active element is connected to an operating element with is arranged on a side of said housing.

11. The apparatus of claim 10, wherein said operating element is designed as an adjusting wheel which has an axis of rotation running approximately transverse to said longitudinal axis of said housing and is in operational connection with said at least one external magnetically active element, a rotary movement of said adjusting wheel causing a movement of said at least one external magnetically active element in an axial direction.

* * * * *